United States Patent [19]

Daoud

[11] Patent Number: 4,920,172
[45] Date of Patent: Apr. 24, 1990

[54] HYDROPHILIC POLYURETHANE EMULSIONS AND MATERIALS PRODUCED THEREFROM

[75] Inventor: Sami Daoud, Flemington, N.J.

[73] Assignee: Tyndale Plains-Hunter Ltd., Princeton, N.J.

[21] Appl. No.: 303,812

[22] Filed: Jan. 30, 1989

[51] Int. Cl.$^5$ .............................................. C08L 75/08
[52] U.S. Cl. .................................... 524/502; 524/591
[58] Field of Search ................................ 524/502, 591

[56] References Cited

U.S. PATENT DOCUMENTS

| | | | |
|---|---|---|---|
| 3,821,136 | 6/1974 | Hudgin et al. | 260/77.5 |
| 3,822,238 | 7/1974 | Blair et al. | 260/75 |
| 3,975,350 | 8/1976 | Hudgin et al. | 260/30.4 |
| 4,202,880 | 5/1980 | Fildes et al. | 424/78 |
| 4,359,558 | 11/1982 | Gould et al. | 525/454 |
| 4,451,635 | 5/1984 | Gould et al. | 528/71 |
| 4,454,309 | 6/1984 | Gould et al. | 525/454 |
| 4,496,535 | 1/1985 | Gould et al. | 424/19 |
| 4,563,490 | 1/1986 | Stol et al. | 524/24 |
| 4,789,720 | 12/1988 | Tettenhart | 528/76 |

FOREIGN PATENT DOCUMENTS 62-057457A  3/1987  Japan.
WO86/05796  10/1986  PCT Int'l Appl..

Primary Examiner—Maurice J. Welsh
Attorney, Agent, or Firm—Ratner & Prestia

[57] ABSTRACT

Solvent-free water-based emulsions of hydrophilic polyurethane polymers, their preparation and solvent-free coatings produced from the emulsions are described. Also described are compositions produced by subjecting a homogeneous blend of a curable polymer precursor such as rubber latex and the polyurethane emulsion to curing conditions. Moisture permeable membranes, water swellable sealants, extruded shapes and active agent media are produced from the composition.

31 Claims, No Drawings

HYDROPHILIC POLYURETHANE EMULSIONS AND MATERIALS PRODUCED THEREFROM

TECHNICAL FIELD

This invention relates to hydrophilic polyurethanes and in particular to aqueous emulsions of water insoluble polyurethanes and their preparation. The invention also pertains to materials and articles, such as films and coatings, produced from such emulsions.

BACKGROUND OF THE INVENTION

Hydrophilic polyurethane polymers are known chemical entities, the description and preparation of which are set forth, for example, in U.S. Pat. Nos. 3,822,238; 3,975,350; 4,156,066; 4,156,067; 4,255,550; 4,359,558 and 4,451,654 incorporated herein by reference.

Such polymers are obtained by reacting a diisocyanate with a resin having two or more reactive terminal hydrogens and containing various polar sites which appear in the final polymer product and are responsible for its hydrophilic character. Illustrative polar sites include ether groups, carboxylic acid groups, sulfhydryl groups, sulfonium groups, sulfonic groups and quaternary ammonium groups.

Representative resin systems from which the hydrophilic polyurethane polymers can be derived are:

1. An adduct of dihydroxy compounds such as ethylene glycol or propylene glycol with ethylene oxide, propylene oxide, ethylenimine, propylenimine, dioxolane or any mixtures of same;
2. An adduct of trihydroxy compounds such as glycerol or trimethylolpropane with ethylene oxide, propylene oxide, ethylenimine, propylenimine, dioxolane or any mixtures of same;
3. An adduct of tetrahydroxy compounds such as erythritol or pentaerythritol with ethylene oxide, propylene oxide, ethylenimine, propylenimine, dioxolane or any mixtures of same;
4. An adduct of polyhydroxy compounds such as anhydroenneaheptitol, sorbitol, mannitol, hydrolyzed low molecular weight polyvinyl acetate, sucrose or lactose with ethylene oxide, propylene oxide, ethylene imine, propylenimine, dioxolane or any mixtures of same;
5. An adduct of polybasic acids such as trimellitic acid, pyromellitic acid, mellitic acid, pyrophosphoric acid, and low molecular weight polyacrylic and methacrylic acids with ethylene oxide, propylene oxide, ethylenimine, dioxolane or any mixtures of same;
6. An adduct of hydroxy acids such as mal eic acid, citric acid or sugar acids with ethylene oxide, propylene oxide, ethylenimine, dioxolane or mixtures of same. Sugar acids are defined in "Carbohydrate Chemistry," Volume 5, and more specifically, Chapter 17 (a review of literature published during 1971), The Chemical Society, Burlington House, London, Great Britain (1972) and in other sources as well;
7. An adduct of amino compounds, such as ammonia, ethylenediamine, diethylenetriamine, triethylenetetramine with ethylene oxide, propylene oxide, ethylenimine, dioxolane or any mixtures of same;
8. Aminium, iminium or quaternary ammonium salts of 7;
9. A sulfonated polyester resin of maleic acid, itaconic acid, mesaconic acid, fumaric acid and a glycol of 2 to 6 carbon atoms;
10. A polyester of a lower alkyl dialkanolamine and a diacid wherein the diacid is adipic, sebacic, azelaic, maleic, phthalic, fumaric acid or mixtures of same, the amine group being converted to an aminium or quaternary ammonium group;
11. A linear or slightly branched polyamide of an alkylamine and a diacid wherein the amine is diethylenetriamine, triethylenetetramine, tetraethylenepentamine or a polyloweralkylenimine such as ethylenimine or propylenimine. Suitable diacids include maleic, adipic, azelaic, sebacic, phthalic, itaconic acid or any mixture of same. The term "slightly branched" indicates only methyl or ethyl substituents on the polyamide backbone, the ethyl substituent being less than 1%.
12. Aminium, iminium or quaternary ammonium salts of 11;
13. Polysulfhydryl resin having in the backbone sulfonium, sulfoxide, or sulfone groups;
14. Iminium, aminium or quaternary ammonium salts of ethylene or propylenimine adducts of polyhydroxy compounds from categories 1 to 4; and
15. Polyesters of polyethylene oxides with maleic acid, adipic acid, sebacic acid, phthalic acid, azelaic acid, fumaric acid or any mixtures of same.

In general, the resins of classes 1–15 above will have an equivalent weight above 140, preferably above 170, and up to about 2000. In addition, a ratio of carbon atoms to oxygen and/or nitrogen atoms ranging from about 1.2:1 to about 2.8:1 is required. Preferably, the ratio is 1.33:1 to 2.8:1, more preferably 1.33:1 to 2.5:1.

Such polyurethane polymers may vary in their hydrophilicity from polymers that are water soluble to polymers which are water insoluble but which nevertheless will absorb water (e.g., at least 10% by weight) usually accompanied by swelling. Hydrophilic character can be controlled by balancing the type and number of polar sites against the type and size of the inert portion of the polymer molecule following the guidelines given in the cited patents.

Articles produced from the hydrophilic polyurethanes aforesaid are commonly formed by a process known as solvent casting. This is a polymer shaping technique in which a solution of the polymer is applied to a substrate or placed in a mold, and the solvent removed by evaporation. There is obtained a durable plastic article having the configuration of the shaping means. For example, moisture permeable film products such as surgical gloves, condoms, surgical dressings, and the like can be produced by spraying a solution of the polyurethane on to the appropriately contoured support and the coating allowed to dry. Multiple sprayings can be applied when making catheters or other articles requiring greater wall thickness.

Where the polyurethane is water insoluble, at least some of the polymer solution will contain an organic solvent. However, the use of organic solvents poses the risk of fire and toxicity hazards which may necessitate the installation of safety devices and equipment to comply with government standards; pollution controls may also be required. All of these preventative measures add considerably to investment in plant capital and increased operating costs. Furthermore, in solvent casting of hydrophilic polyurethane polymers, it is difficult to remove all traces of solvent. Consequently, the end polymer product tends to retain a small amount of residual solvent. This can be a problem in certain sensitive areas of use, such as where the solvent cast polyurethane article is placed in contact with body tissues which can become irritated by leaching out of the solvent. For instance, the presence of solvent residue in articles for use as catheters, implants, condoms and the like is undesirable.

Clearly there is a need for producing castings of water insoluble hydrophilic polyurethane polymers which do not require the use of an organic solvent.

One possible approach would be to employ the polyurethane in the form of an aqueous emulsion. It is, of course, well known to form polymer emulsions by conducting the polymerization in an aqueous medium. However, this procedure is not practical for preparing aqueous emulsions of a hydrophilic polyurethane since the reactants from which the polymer is synthesized are not compatible with an aqueous medium; the diisocyanate reacts with water and the polyol is soluble in water.

SUMMARY OF THE INVENTION

It is, accordingly, an object of the present invention to provide solvent-free water-based emulsions of water insoluble hydrophilic polyurethane polymers. It is a further object of the invention to provide shaped polymer articles formed from said polyurethane emulsions by solventless casting. It is a still further object of the invention to provide blends of said emulsions with other aqueous polymer systems and to shaped articles formed from solventless casting of said blends. Other objects and purposes of the invention will become apparent in the ensuing description.

DETAILED DESCRIPTION

The water-based hydrophilic polyurethane emulsions of the invention are realized by first forming a solution of a water insoluble hydrophilic polyurethane in a water immiscible, relatively inert, normally liquid organic solvent. Desirably, the solvent has a boiling point below that of water, generally in the range of from about 20° C. to about 85° C. A preferred solvent is a chlorinated aliphatic hydrocarbon such as methylene chloride or chloroform.

In the next step of the process, the solvent solution of polyurethane is added, with vigorous agitation, to an aqueous dispersing medium containing a surfactant such as sodium alkylbenzenesulfonate or sodium alkylsulfate. The aqueous medium may also contain a defoamer and a bactericidal or fungicidal agent.

After introduction of the solvent solution, the resulting dispersion is subjected to conditions for removal of the organic solvent in order to form an emulsion of the solvent-free polyurethane in the aqueous medium. This step is implemented by placing the dispersion in a shallow vessel and while stirring at about room temperature, a stream of air is blown across the surface of the dispersion to drive off the solvent.

The hydrophilic polyurethane water-based emulsions of the invention are opaque liquids, off-white in color and exhibit viscosities in the range of from about 3,000 to about 4,000 cp. Such emulsions are characterized by excellent stability, test specimens having been stored several months at temperatures between 5° to 95° C. without deterioration or loss of properties.

The concentration of polymer in the water-based emulsion is not especially critical although there are certain practical limits. For instance, some hydrophilic polyurethanes may form highly viscous emulsions which are difficult to handle. Other polymers may be employed at fairly high levels to give workable emulsions. Concentration of the polymer is also dictated by the wall thickness of the cast article. Usually, the water-based polyurethane emulsions of the invention will have a polymer content constituting about 5% to about 15% by weight of the emulsion composition.

So far as can be ascertained, water-based, hydrophilic polyurethane polymer emulsions can be produced by the process of the invention from any water insoluble, hydrophilic polyurethane which can be dissolved in a water immiscible organic solvent of the type as previously defined. Generally suitable are the hydrophilic water insoluble, water swellable polyurethanes disclosed in the aforecited patents. Polymers of this type with water content (at equilibrium with water) between 15% and 85% have been successfully prepared as water-based emulsions according to the invention.

Since they are free of solvents, which can act as sensitizers or irritants to the skin or tissues, the herein emulsion polyurethane polymers are well-suited for use in the manufacture of cosmetics and biomaterials such as wound dressings, barrier coatings and the like.

The polymer emulsions may include an active agent, examples of which are germicides, insecticides, spermicides, insect repellants, detergents, various drugs and medicines, cosmetics, fragrances, flavors, etc. On exposure of films and articles cast from the emulsions to a moist environment, the active agent is released.

Compared with solvent-based polymer solutions of hydrophilic polyurethanes, the choice of active agents is wider when water-based emulsions of the polymers are employed, owing to the fact that both water soluble and solvent soluble active agents can be used.

A representative polyurethane component of the herein water-based emulsion is a hydrophilic, water insoluble polyurethane having a number average molecular weight of from about 10,000 to about 200,000. It is prepared by reacting, at an NCO/OH ratio of about 0.75 to 1.05, preferably about 0.85 to 0.98, an organic diisocyanate with a glycol blend of a polyoxyethylene glycol having a number average molecular weight of from about 400 to about 20,000 and a low molecular weight glycol as typified by ethylene glycol and diethylene glycol; optional amounts of a higher polyoxyalkylene glycol in which the alkylene unit contains 3 to 4 carbon atoms may supply part of the OH equivalent. Sufficient water is included to produce foaming of the polyurethane polymer. The reaction is catalyzed by known catalysts, examples of which are tin salts and organic tin esters such as dibutyltin dilaurate.

The degree of hydrophilic character which generally determines the moisture permeability of the polyurethane polymer can be controlled by adjusting the ratio of polyoxyethylene glycol to the higher polyoxyalkylene glycols. The former imparts hydrophilicity; the latter imparts hydrophobicity.

Exemplary aliphatic and aromatic diisocyantes that can be used in preparing the hydrophilic polyurethane polymers aforesaid are 4,4'-methylene-bis(cyclohexylisocyanate), 1,4-tetramethylenediisocyanate, 1,4-cyclohexylenediisocyanate and aromatic diisocyanates such as toluene -2,4- and -2,6- diisocyanates. Also suitable are the isocyanate equivalents which form urethane linkages as typified by nitrile carbonates such as adiponitrile carbonate.

The alkylene glycols and polyoxyalkylene glycols are known entities which are available from chemical supply houses and manufacturers. Typical commercial products are diethylene glycol and a line of polyoxyethylene glycol resins sold by the Union Carbide Corporation under the trademark CARBOWAX®, such as CARBOWAX® 1450, CARBOWAX® 4500 and CARBOWAX® 8000. The numbers refer to average molecular weights.

Also available commercially are the higher polyoxyalkylene glycols. For instance, polyoxypropylene glycols containing repeating isopropylene ether [—$OCH_2CH(CH_3)$—] groups, such as the PPG series of NIAX® polyether polyols, are sold by the Union Carbide Corporation. In the NIAX® product designations, the numbers refer to average molecular weight. Thus, NIAX® PPG1025 polyoxypropylene glycol has a number average molecular weight of 1025. Other NIAX® polyether polyols include PPG-425, PPG-725, PPG-1225 and PPG-2025.

Polyoxytetramethylene glycol is also a known polymer material that is commercially produced under the trademark and designation TERATHANE® sold by the E. I. Dupont de Nemours and Co. TERATHANE® encompasses a brand of polyoxytetramethylene glycols of the formula $HO(CH_2CH_2CH_2CH_2O)_nH$ where n is an integer of from about 9 to 40. Representative products are TERATHANE® 1000, n=14 and TERATHANE® 2000, n=27. These are a blend of linear diols, in which the terminal OH groups are separated by repeating tetramethylene ether (—$OCH_2CH_2CH_2CH_2$—) groups.

The solvent free water-based hydrophilic polyurethane polymer emulsions of the invention can be combined with other solventless polymers or polymer precursors to give a variety of composite polymer products having useful properties. For instance, tacky and adhesive coatings are obtained by applying, to a substrate, a mixture of the herein polyurethane emulsions and an aqueous solution or dispersion of a polymer followed by evaporation of the aqueous medium. Excellent tacky coatings have been produced using water dispersions of hydrophobic polyurethane polymers. The procedure and choice of components is patterned after the known technique of forming such coatings from solvent solutions.

Polymer composites which are thermosetting in nature are obtained by first forming a blend of the polyurethane emulsion and a polymer precursor, plus a curing agent. Water is then removed and the stripped blend pressure formed or extruded to give the desired shape. In the case of films or membranes, such as condoms or gloves containing a curable rubber component, dipping or casting is the usual forming method. Once the final configuration is obtained, curing is effected by application of heat.

Exemplary curing agents include sulfur, zinc oxide, dimethyl zinc, methyl and ethyl dithiocarbonate.

Representative heat curable polymer precursors include monomers, prepolymers and latices of various polymers which are capable of further polymerization or curing such as rubber, vinyl and acrylic latices. The curable rubber components embrace both uncured natural rubber as well as various synthetic curable rubber components commonly used in the preparation of synthetic rubbers and elastomers. Representative synthetic rubber components include those derived from unsaturated hydrocarbon monomers and mixtures thereof, such as isoprene, chloroprene, butadiene, SBT (styrene/butadiene/rubber), isobutene/isoprene and EPDM (ethylene/propylene/butadiene). Synthetic rubber monomers and latices produced therefrom, as well as other chemicals used in the manufacture of rubber and useful in the invention, are well known and are commercialy available from a number of chemical suppliers.

A generally preferred composite polymer material is obtained by casting a heat curable blend of an aqueous dispersion of a hydrophobic polymer forming precursor of the type aforesaid and a water-based emulsion of a water insoluble, hydrophilic polyurethane polymer of the invention as previously described. The polymer precursor imparts hydrophobic and rubbery character to the composite polymer and should be present on a solids weight basis in the blend of at least about 30% up to about 90%. By keeping within this range, other physical properties of the composite, i.e., modulus, hardness, tear resistance, tensile strength and elasticity will be generally satisfactory.

The composite polymer materials can be cast into articles of the requisite moisture absorptivity and film products having controlled moisture transmission such as prophylatic devices (pessaries and condoms), surgical gloves, surgical membranes and dressings and the like. Moisture permeability is controlled by adjusting the ratio of hydrophilic polyurethane to hydrophobic polymer. Coatings can be prepared by spraying a substrate or shaped article with the aqueous blend of curable components and the coatings cured in place. The composite polymers can also be cast, extruded, pressed, calendered or molded into a variety of useful shapes and configurations such as rods, bulk articles and tubing (for example, surgical catheters).

A further use of these composite materials is as an active release medium in the same manner as above described for polymers produced from the water-based polyurethane polymer emulsions alone.

The water-based hydrophilic polyurethane polymer emulsions of the invention are useful in preparing improved solvent-free, moisture-sensitive rubber compositions described in pending Ser. No. 108,423, filed 10/14/87 to Faust et al. and presently assigned to the assignee of record.

Reference is now made to the following examples in which components are given in parts by weight unless stated otherwise.

PREPARATION OF SOLVENT-FREE WATER-BASED HYDROPHILIC POLYURETHANE EMULSIONS AND FILMS PRODUCED THEREFROM

EXAMPLE 1

A hydrophilic polyurethane polymer was prepared by mixing 11.41 parts of CARBOWAX® 1450 (Union Carbide), 7.87 parts of CARBOWAX® 1000, 4.72 parts of CARBOWAX® 600, 3.15 parts of CARBOWAX® 400, 24.41 parts of TERATHANE® 2000 (Dupont), 6.05 parts of ethylene glycol and 0.38 parts of water. The preceding components were heated to 60° C. in order to melt the polyols, then mixed well, and finally combined with 42.01 parts of Desmodur W, 4,4'-methylene-bis(cyclohexylisocyanate) (Mobay). Into the reaction mixture were added 0.12 parts of stannous octoate and the mass allowed to exotherm to 70° C., when it was poured into a polypropylene tray and cured at 100° C. for one hour in a hot air circulating oven. The finished polymer was granulated to ¼ inch size granules.

A 10% solids solution of the polymer was prepared by dissolving 140 part of the granulated polymer in 1260 parts of dichloromethane. An aqueous solution was prepared by dissolving 2.8 parts of sodium lauryl sulfate surfactant in 1,000 parts of water which was thoroughly mixed with 0.28 parts of SAG-10 defoamer (Union Carbide) and 0.1 parts of Germaben II bacteriostatic agent (Sutton Laboratories).

While stirring the aqueous solution vigorously, the polymer solution in dichloromethane was added slowly and continuously. The stirring was continued 2 minutes after the last of the polymer solution was added.

The resulting dispersion was transferred to a flat glass container and stirred at room temperature under an air current to remove all of the solvent. The resulting aqueous hydrophilic polyurethane emulsion was an off-white opaque liquid with a viscosity of 2,450 cP at 25° C.

Films were cast from both the solvent solution of the polymer and from the solvent-free water-based emulsion, onto flat, Teflon-coated pans. After air-drying, the film cast from the emulsion was dried at 80° C. for 30 minutes. The water content, expansion on swelling and mechanical properties of both films were measured side-by-side:

TABLE 1

| Property | Film | |
|---|---|---|
| | Emulsion Cast | Solvent Cast |
| Water Content (%) | 23.1 | 24.8 |
| Expansion (%) | 12.0 | 10.9 |
| Mechanical Properites (DRY/WET) | | |
| Tensile Strength (psi) | 1844/1924 | 3693/2823 |
| 100% Secant Modulus (psi) | 253/270 | 270/392 |
| Elongation at Break (%) | 425/500 | 420/460 |
| Tear Resistance (lb/in) | 98/86 | 200/140 |

Water content is the amount of water (%) in the polymer swollen to equilibrium in distilled water. Expansion (%) is the increase in linear length on swelling to equilibrium. Mechanical properties were measured according to ASTM-638-84 (tensile) and ASTM 1004-66 (tear).

The resulting films had a water vapor permeability (0–100% humidity, 37° C.) of 640/g/m²/24 hours, and are therefore suitable for manufacture of protective gloves which allow the breathing of the skin, i.e., sufficient passsage of skin generated water vapor to prevent the water logging of the skin.

EXAMPLE 2

A hydrophilic polyurethane was prepared by mixing 11.71 parts of CARBOWAX® 1450, 7.66 parts of CARBOWAX® 1000, 4.60 parts of CARBOWAX® 600, 3.06 parts of CARBOWAX® 400, 23.24 parts of NIAX PPG 1025 (Union Carbide), 6.18 parts of ethylene glycol and 0.38 parts of water. The mixture was heated during stirring to 60° C. and homogenized. 43.77 parts of Desmodur W was added and finally, 0.16 parts of stannous octoate catalyst. The mixture exothermed to 70° C., when it was poured into a polypropylene tray and cured at 100° C. for one hour. The resulting polymer was granulated.

140 parts of the polymer from Example 2 were dissolved in 1260 parts of dichloromethane.

2.8 parts of sodium lauryl sulfate, 0.28 parts of SAG-10 defoamer and 0.10 parts of methyl paraben bacteriostat were dissolved in 1,000 parts of water. The aqueous hydrophilic polyurethane emulsion was prepared as described in Example 1.

Films were cast both from the solvent solution and from the water-based emulsion of the polymer. Their properties were as follows:

TABLE 2

| Property | Film | |
|---|---|---|
| | Emulsion Cast | Solvent Cast |
| Water Content (%) | 33.1 | 30.7 |
| Expansion (%) | 18.0 | 11.4 |
| Mechanical Properties DRY/WET | | |
| Tensile Strength (psi) | 4548/2297 | 4317/3510 |
| 100% Secant Modulus (psi) | 248/265 | 200/313 |
| Elongation at Break (%) | 575/675 | 495/600 |
| Tear Resistance (lb/in) | 149/126 | 213/117 |

The films cast from both the solvent solution and from the solvent-free emulsion are suitable for dipping condoms, because while possessing in the wet state similar properties to rubber latex, they have much improved sensitivity, no smell and more natural (slippery) feel in the wet state.

Such emulsion-based films are also very good skin coverings, without or with active ingredients. They can be used in cosmetics as fragrance carriers, skin emollient carriers, or carriers for insecticides or antiperspirants. In veterinary medicine, they are excellent carriers for ektoparasiticides, for example cyhalotrin [α-cyano-3-phenoxybenzyl-(Z)-(1RS,3RS)-3-(2-chloro-3,3,3-trifluoropropenyl)-2,2-dimethylcyclopropanecarboxylate], which can be added in amounts of up to 30% by weight of the dry polymer.

EXAMPLE 3

A hydrophilic polyurethane was prepared by reacting 55.50 parts of CARBOWAX® 1450, 8.84 parts of diethylene glycol, 0.27 parts of water and 35.39 parts of Desmodur W and 0.10 parts of stannous octoate as described in Examples 1 and 2. The finished polymer was granulated.

An emulsion was prepared as described in Example 1. Its viscosity was 1740 cP at 25° C. and it contained 15% solids.

The cast polymeric film had a water content of 54.0%, expansion of 43.0% and water vapor transmission rate of 1,400 g/m²/24 hours. Its wet properties were: tensile strength 504 psi, 100% secant modulus 36 psi, elongation 700% and tear resistance 41 lb/in.

Because of its high water vapor transmission rate, these polymeric films are extremely suitable for wound and skin covering, protective skin coatings, and as carriers of drugs, fragrances and other active ingredients.

EXAMPLE 4

A hydrophilic polyurethane was prepared according to Example 1 by reacting 84.83 parts of CARBOWAX® 8000, 2.38 parts of diethylene glycol, 0.48 parts of water and 12.31 parts of Desmodur W. The finished polymer was granulated.

An emulsion was prepared following the procedure described in Example 1. The resulting emulsion had a viscosity of 3,900 cP at 25° C. and 14% solids content.

The cast film had a water content of 88.6% and expansion of 114.2%. Its water vapor transmission rate was almost 3,000 g/m²/24 hours, and its surface when in swollen state was extremely slippery. Thus, these films are highly suitable as slippery hydrophilic coatings on medical devices such as catheters, implants and tendon sheats.

Their slipperiness is of advantage also in certain industrial coatings, like boat coatings, coatings of the insides of pipes to lower their drag and increase throughput, etc.

EXAMPLE 5

A hydrophilic polyurethane was prepared according to Example 1, by reacting 10.89 parts of CARBOWAX® 1450, 7.50 parts of CARBOWAX® 1000, 4.51 parts of CARBOWAX® 600, 3.00 parts of CARBOWAX® 400, 19.65 parts of NIAX PPG 1025, 7.19 parts of ethylene glycol, 0.39 parts of water and 46.87 parts of Desmodur W. The cured polymer was granulated.

A solution of the polymer was prepared by dissolving 8 parts of the polymer in 92 parts of chloroform. The resulting solution was slowly and gradually added under vigorous stirring into a solution of 0.3 parts of ZONYL FSA fluorosurfactant (DuPont) and 0.05 parts of SAG-10 defoamer in 80 parts of distilled water. The resulting dispersion was placed into a rotary evaporator and the solvent stripped at 45° C. over 10 hours.

A film was cast from the so obtained aqueous, solvent-free polyurethane emulsion in a covered pan, air dried and cured at 100° C. for 30 minutes. Its properties were compared to a film cast from the solvent solution and air-dried:

TABLE 3

| Property | Film Emulsion Cast | Film Solvent Cast |
|---|---|---|
| Water Content (%) | 27.6 | 29.0 |
| Expansion (%) | 12.8 | 13.8 |
| Mechanical Properties DRY/WET | | |
| Tensile Strength (psi) | 5224/2385 | 5276/4058 |
| 100% Secant Modulus (psi) | 568/216 | 719/348 |
| Elongation at Break (%) | 475/450 | 485/500 |
| Tear Resistance (lb/in) | 303/106 | 238/228 |

The resulting film, due to its excellent mechanical properties, is suitable for manufacturing condoms, pessaries, "breathing" gloves, wound and skin protective covers, and also as a carrier of active ingredients both in cosmetics (fragrances, emollients, antiperspirants) and medicine (drugs, medications) and in veterinary applications (insecticides, pesticides, drugs).

EXAMPLE 6

A hydrophilic polyurethane was prepared by mixing 54.38 parts of CARBOWAX® 1450 and 7.14 parts of diethylene glycol and heating the mixture to 90° C. 2.39 parts of -glucone lactone were added and mixed until dissolved. The reactants were cooled to 60° C. and 0.27 parts of water and 35.82 parts of Desmodur W were added and mixed well. Finally, 0.15 parts of dibutyltin dilaurate catalyst were added. The mixture exothermed to 75° C., at which stage it was poured into polypropylene trays and cured at 100° C. for 15 minutes. The resulting polymer was granulated.

100 parts of the polymer granules were suspended in 400 parts of methanol and 25 parts of 10% sodium hydroxide solution in water were added. The mixture was rolled for 8 hours during which time the polymer dissolved. Sufficient 10% hydrochloric acid was added to bring the pH of the solution to 8. The mixture was filtered and poured into 2,000 parts of distilled water.

The precipitated polymer was strained from the water and dried at 40° C. to constant weight.

20 parts of the polymer were dissolved in 80 parts of Dichloromethane. This solution was gradually added with vigorous stirring into a solution of 1.5 parts of sodium lauryl sulfate and 0.5 parts of SAG-10 defoamer in 100 parts of distilled water. The resulting dispersion was placed in a suitable container and the solvent removed in vacuo (5–8 mm Hg) at 30° C. to give a solvent-free, aqueous polyurethane emulsion.

The polymer contains carboxy groups and is therefore suitable as coating on pills or capsules containing drugs whose absorption window is in the stomach.

Since polymers containing carboxy groups have been proven to adhere to the stomach wall, the drug is kept in the stomach for up to 16 hours, achieving thus a regulated slow release.

The polymer also exhibits excellent adhesion for a host of other substrates, and is therefore suitable for boat hulls coating, coating of medical devices, as catheters and sensors, and for veterinary applictions where adhesion to the tissues or mucosa is needed.

EXAMPLE 7

Aqueous Emulsions Prepared from Cross-linked Hydrophilic Polyurethanes

A hydrophilic polymer emulsion was prepared as described in Example 2. To the emulsion was added, as cross linkers, glyoxal or Uformite 27-806 (ureaformaldehyde resin, manufactured by Reichhold, Detroit, Mich.). Both were used in the ratio of 2 parts per 100 parts of polymer. The parts are on a solids weight basis.

Curing temperature of the mixture was 100° C. and curing times were 15 and 30 minutes. Cured films were compared with identical uncured film, As shown in the following table, cross linking results in improved mechanical properties.

TABLE 4

| | (PROPERTIES WET) | | | |
|---|---|---|---|---|
| FILM (cure time) | TENSILE STRENGTH (psi) | ELONGATION (%) | MODULUS 100% (psi) | TEAR RES. (lb/in) |
| no cure 15 min. | 1,715 | 550 | 189 | 71 |
| no cure 30 min. | 1,691 | 500 | 249 | 62 |
| Glyoxal 15 min. | 2,340 | 550 | 211 | 100 |
| Glyoxal 30 min. | 2,307 | 500 | 189 | 97 |
| Uformite 15 min. | 2,404 | 516 | 265 | 107 |
| Uformite 30 min. | 1,947 | 500 | 474 | 66 |

EXAMPLE 8

An emulsion was processed with the crosslinking agents as described in Example 7, only this time a coagulation agent was used for the dipping. The mandrels were dipped first in 1% alcoholic solution of calcium nitrate, air-dried and then dipped in the emulsion, dried and cured as before. The coagulating agent improved the coagulation of the emulsion and helped to fuse the polymer particles together.

TABLE 5

| FILM (CURE TIME) | TENSILE STRENGTH (PSI) | ELONGATION (%) | MODULUS 100% (psi) | TEAR RES. (lb/in) |
|---|---|---|---|---|
| no cure 15 min. | 2,230 | 675 | 164 | 97 |
| no cure 15 min. | 2,241 | 700 | 183 | 90 |
| Glyoxal 15 min. | 2,390 | 650 | 276 | 99 |
| Glyoxal 30 min. | 2,852 | 550 | 167 | 109 |
| Uformite 15 min. | 2,900 | 600 | 198 | 107 |
| Uformite 30 min. | 2,702 | 600 | 329 | 112 |
| Solvent cast | 3,510 | 600 | 313 | 117 |

(Wet Values)

Both curing agents and coagulating agents improve mechanical properties, especially tensile strength and tear resistance. Time of cure does not appear to be critical but cure temperatures much below 100° C. may lead to a reduction in mechanical strength.

POLYMER COMPOSITES AND FILMS PRODUCED THEREFROM

EXAMPLE 9

A hydrophilic polyurethane polymer was prepared by mixing 11.41 parts of CARBOWAX® 1450, 7.87 parts of CARBOWAX® 1000, 4.72 parts of CARBOWAX® 600, 3.15 parts of CARBOWAX® 600, 3.15 parts of CARBOWAX® 400, 24.41 parts of TERATHANE® 2000, 6.05 parts of ethylene glycol and 0.38 parts of water. The preceding components were heated to 60° C. to melt the polyols, mixed well and finally mixed with 42.01 parts of Desmodur W. Into the reaction mixture were added 0.12 parts of stannous octoate and the mass allowed to exotherm to 70° C. after which it was poured into a polypropylene tray and cured at 100° C. for one hour in a hot air circulating oven.

The finished polymer was granulated to ¼ inch size granules.

A 10% solids solution of the polymer was prepared by dissolving 140.0 parts of the granulated polymer in 1260.0 parts of dichloromethane. This solution was slowly added with vigorous agitation to 1000 parts of water mixed with 2.8 parts of sodium lauryl sulfate surfactant and 0.28 parts of SAG-10 defoamer and 0.10 parts of Germaben II bacteriostatic agent, a mixture of imidazolidinyl urea, methyl and propyl paraben. Stirring was continued for 2 minutes after the polymer solution was added.

The mixture was transferred to a flat glass container and stirred at room temperature under an air current to remove all the solvent. The resulting hydrophilic polyurethane emulsion is an off-white opaque liquid with a viscosity of 2450 cp at 25° C.

To 35 parts of the above prepared emulsion were added 65 parts of natural rubber latex (50% solids). The blend was mixed well; a film was cast, cured and tested. Results are recorded below.

| (DRY/WET) | |
|---|---|
| Tensile Strength (psi) | 4000/2100 |
| Elongation (%) | 520/500 |
| Tear Resistance (lb/in) | 320/190 |
| Tear Propagation (lb/in) | 92/62 |
| Tensile Stress (psi) | |
| 50% | 300/180 |
| 100% | 400/200 |
| 300% | 1600/900 |
| 500% | 1800/1200 |

EXAMPLE 10

A hydrophilic polyurethane was prepared by mixing 11.71 parts of CARBOWAX® 1450, 7.66 parts of CARBOWAX® 1000, 4.60 parts of CARBOWAX® 600, 3.06 parts of CARBOWAX® 400, 23.24 parts of NIAX PPG 1025, 6.18 parts of ethylene glycol and 0.38 parts of water. The mixture was heated under stirring to 60° C. until thoroughly blended. 43.77 parts of Desmodur W were added and finally, 0.16 parts of stannous octoate catalyst. The mixture exothermed and was poured into a polypropylene tray and cured at 100° C. for 1 hour. The resulting polymer was then granulated.

140 parts of the polymer were dissolved in 1260 parts of dichloromethane and the solution dispersed in 1000 parts of water mixed with 2.8 parts of sodium lauryl sulfate, 0.28 parts of SAG-10 defoamer and 0.10 parts of methyl paraben. The emulsion was prepared as described in Example 9.

To 35 parts of the emulsion was added 65 parts of natural rubber latex (50% solids).

The blend was well mixed and a film cast, cured and then tested. Results are recorded below.

| (Dry/Wet) | |
|---|---|
| Tensile Strength (psi) | 4300/2600 |
| Ult. elongation (%) | 550/550 |
| Tensile Stress (psi) | |
| 50% | 450/270 |
| 100% | 800/500 |
| 300% | 2500/1500 |
| 500% | 3100/2100 |
| Water Content (%) | 14.2 |
| Expansion (%) | 5.1 |
| Leachables (in water)* (%) | 4.1 |
| MVTR (g/m$^2$/24 hr.) | 401 |

*10 parts of polymer in 90 parts of water, mixed, room temperature, 48 hours.

EXAMPLE 11

A styrene/butadiene latex was prepared as follows: To 72.4 parts of 69% solids Pliolite 5345 synthetic styrene/butadiene rubber latex (Goodyear Co.) were added 1.1 parts of 60% solids sulfur dispersion, 0.6 parts of 60% solids zinc oxide dispersion, 0.8 parts of 50% solids ethyl zimate (zinc diethyldithiocarbamate) dispersion (R. T. Vanderbilt Co.) and 56.2 parts of water.

To 65.0 parts of the styrene/butadiene latex prepared above were added 35 parts of the emulsion of Example 9. The blend was well mixed, a film was cast, cured and tested. The test results are given below.

| DRY/WET | |
|---|---|
| Tensile Strength (psi) | 3200/2100 |
| Elongation (%) | 600/550 |
| Tear Resistance (lb/in) | 290/170 |
| Tear Propagation (lb/in) | 89/52 |
| Tensile Stress (psi) | |
| 50% | 150/89 |
| 100% | 220/170 |

-continued

| | |
|---|---|
| 300% | 370/245 |

EXAMPLE 12

To 70 parts of RA/2333 GELVA® multipolymer acrylic adhesive emulsion (Monsanto Co.) was added 30 parts of the emulsion from Example 10. The blend was well mixed and a film was cast and found to possess an excellent strength and high tack. (Peel strength is 0.6 kg/cm.)

EXAMPLE 13

To 90 parts of the emulsion from Example 10 was added 10 parts of Baybond XW-116 blocked water reducible aliphatic polyisocyanate (made by Mobay Corp.).

A film of the blend was cast, cured and tested. The test data is summarized below.

| DRY/WET | |
|---|---|
| Tensile Strength (psi) | 4800/2920 |
| Elongation (%) | 650/600 |
| Tensile Stress (psi) | |
| 50% | 290/110 |
| 100% | 440/290 |
| 300% | 1000/600 |
| 500% | 3000/900 |
| Tear Resistance (lb/in) | 250/170 |
| Tear Propagation (lb/in) | 90/40 |

EXAMPLE 14

To 80 parts of the emulsion from Example 10 was added 10 parts of Baybond XW-114 anionic aliphatic hydrophobic polyurethane dispersion (made by Mobay Corp.).

The blend well mixed, a film was cast and dried. The film was tested and the results given below.

| WET | |
|---|---|
| Tensile Strength (psi) | 4400 |
| Ult. Elongation (%) | 520 |
| 100% Modulus (psi) | 500 |
| Tear Resistance (lb/in) | 355 |
| Tear Propagation (lb/in) | 130 |

The foregoing has set forth an exemplary and preferred embodiment of the present invention. It will be understood, however, that various alternatives will occur to those of ordinary skill in the art without departure from the spirit and scope of the present invention.

What is claimed:

1. An aqueous emulsion of a hydrophilic polyurethane produced by the steps of:
   a. dissolving a water insoluble hydrophilic polyurethane in a water immiscible, organic solvent having a boiling point below 100° C.;
   b. forming a dispersion of the solution from a. in water by adding the solution to water in the presence of a surfactant while maintaining sufficient agitation to effect dispersal of the solution; and
   c. evaporating the organic solvent component of the dispersion, thereby forming a solvent-free emulsion of the polyurethane in the aqueous medium.

2. An aqueous emulsion of a hydrophilic polyurethane produced by the steps of:
   a. providing a water insoluble hydrophilic polyurethane of number average molecular weight of from about 10,000 to about 200,000, by reacting at an NCO/OH ratio of from about 0.75 to about 1.05, an organic diisocyanate with a glycol mixture of polyoxyethylene glycol of number average molecular weight of from about 400 to about 20,000 and a lower molecular weight glycol selected from the class consisting of ethylene glycol and diethylene glycol, in the presence of sufficient water to promote foaming of the polymer, it being provided that part of the glycol mixture can be replaced by optional equivalents of a polyoxyalkylene glycol selected from the class consisting of polyoxypropylene glycols of number average molecular weight of from about 200 to about 2500 and polyoxytetramethylene glycols of number average molecular weight of from about 650 to about 3000;
   b. dissolving the polymer from step a. in a water immiscible organic solvent having a boiling point below 100° C.;
   c. forming a dispersion of the solution from b. in water by adding the solution while maintaining sufficient agitation to effect dispersal of the solution; and
   d. evaporating the solvent component of the dispersion, thereby forming a solvent free emulsion of the polyurethane in the aqueous medium.

3. A composition of claim 2 wherein the boiling point of the organic solvent is between about 20° C. and about 85° C.

4. A composition of claim 2 wherein the solvent is an aliphatic chlorinated hydrocarbon.

5. A composition of matter comprising a homogeneous aqueous blend of a polymer or heat curable polymer precursor and an aqueous emulsion of a water insoluble hydrophilic polyurethane having a number average molecular weight of from about 10,000 to about 200,000 prepared by reacting at a NCO/OH ratio of from about 0.75 to about 1.05, an organic diisocyanate and a glycol blend of a polyoxyethylene glycol having a number average molecular weight of from about 400 to about 20,000 and a lower molecular weight glycol plus sufficient water to produce foaming of the polymer, it being optionally provided that part of the OH equivalents may be supplied by a higher polyoxyalkylene glycol in which the alkylene units contain 3 to 4 carbon atoms, the said water-based emulsion being produced by the steps of:
   a. forming a solution of the hydrophilic polyurethane in a water immiscible organic solvent having a boiling point below 100° C.;
   b. forming a dispersion of the solution from a. in water by adding the solution to water in the presence of a surfactant while maintaining sufficient agitation to effect dispersal of the solution, and
   c. evaporating the organic solvent component of the dispersion, thereby leaving a solvent-free emulsion of the polyurethane in the aqueous medium.

6. A composition of claim 5 wherein the polymer precursor is selected from the class consisting of rubber, vinyl, and acrylic latices.

7. A composition of claim 6 wherein the polymer precursor is present on a solids weight basis of from about 30% to about 90%.

8. A composition of claim 5 wherein the organic solvent is an aliphatic chlorinated hydrocarbon.

9. An article formed from a composition of claim 2.

10. An article of claim 9 which is cured.

11. An article of claim 10 which is a coating, a film, a membrane, or an extruded or molded object.

12. An article of claim 11 which is in the form of a tube or a cannula.

13. An article of claim 11 which is a prophylactic device, a bandage, a surgical drape, a glove or a catheter.

14. A sealant prepared from a composition of claim 2.

15. An article formed from a composition of claim 5.

16. An article of claim 15 which is cured.

17. An article of claim 16 which is a coating, a film, a membrane, or an extruded or molded object.

18. An article of claim 17 which is in the form of a tube or a cannula.

19. An article of claim 17 which is a prophylactic device, a bandage, a surgical drape, a glove or a catheter.

20. A sealant prepared from a composition of claim 5.

21. An active agent release medium comprising an active agent and a composition of claim 1.

22. An active agent release medium of claim 21 wherein the active agent is a drug.

23. An active agent release medium of claim 21 wherein the active agent is a fragrance.

24. An active agent release medium of claim 21 wherein the active agent is a cosmetic.

25. An active agent release medium of claim 21 wherein the active agent is a biocide.

26. An active agent release medium of claim 25 wherein the biocide is a germicide, an insecticide or a spermicide.

27. An active agent release medium of claim 21 wherein the active agent is an insect repellant.

28. An active agent release medium of claim 21 wherein the active agent is a detergent.

29. A method for preparing an aqueous emulsion of a water insoluble hydrophilic polyurethane, comprising the steps of:
  a. dissolving a water insoluble hydrophilic polyurethane in a water immiscible, organic solvent having a boiling point below 100° C.;
  b. forming a dispersion of the solution from a. in water by adding the solution to water in the presence of a surfactant while maintaining sufficient agitation to effect dispersal of the solution; and
  c. evaporating the organic solvent component of the dispersion, thereby forming a solvent-free emulsion of the polyurethane in the aqueous medium.

30. A method for preparing an aqueous emulsion of a water insoluble hydrophilic polyurethane comprising the steps of:
  a. providing a water insoluble hydrophilic polyurethane of number average molecular weight of from about 10,000 to about 200,000, by reacting at an NCO/OH ratio of from about 0.75 to about 1.05, an organic diisocyanate with a glycol mixture of polyoxyethylene glycol of number average molecular weight of from about 400 to about 20,000 and a lower molecular weight glycol selected from the class consisting of ethylene glycol and diethylene glycol, in the presence of sufficient water to promote foaming of the polymer, it being provided that part of the glycol mixture can be replaced by optional equivalents of a polyoxyalkylene glycol selected from the class consisting of polyoxypropylene glycols of number average molecular weight of from about 200 to about 2500 and polyoxytetramethylene glycols of number average molecular weight of from about 650 to about 3000;
  b. dissolving the polymer from step a. in a water immiscible organic solvent having a boiling point below 100° C.;
  c. forming a dispersion of the solution from b. in water by adding the solution while maintaining sufficient agitation to effect dispersal of the solution; and
  d. evaporating the organic solvent component of the dispersion, thereby forming a solvent free emulsion of the polyurethane in the aqueous medium.

31. A method for preparing a homogeneous aqueous blend of a polymer or heat curable polymer precursor and an aqueous emulsion of a water insoluble hydrophilic polyurethane comprising the steps of:
  a. providing a water insoluble hydrophilic polyurethane of number average molecular weight of from about 10,000 to about 200,000, by reacting at an NCO/OH ratio of from about 0.75 to about 1.05, an organic diisocyanate with a glycol mixture of polyoxyethylene glycol of number average molecular weight of from about 400 to about 20,000 and a lower molecular weight glycol selected from the class consisting of ethylene glycol and diethylene glycol, in the presence of sufficient water to promote foaming of the polymer, it being provided that part of the glycol mixture can be replaced by optional equivalents of a polyoxyalkylene glycol selected from the class consisting of polyoxypropylene glycols of number average molecular weight of from about 200 to about 2500 and polyoxytetramethylene glycols of number average molecular weight of from about 650 to about 3000;
  b. dissolving the polymer from step a. in a water immiscible organic solvent having a boiling point below 100° C.;
  c. forming a dispersion of the solution from b. in water by adding the solution while maintaining sufficient agitation to effect dispersal of the solution; and
  d. evaporating the organic solvent component of the dispersion, thereby forming a solvent free emulsion of the polyurethane in the aqueous medium.
  e. adding a polymer or polymer precursor latex to the emulsion.

* * * * *